(12) United States Patent
Breton et al.

(10) Patent No.: US 6,521,239 B1
(45) Date of Patent: Feb. 18, 2003

(54) COSMETIC COMPOSITION CONTAINING AT LEAST ONE AUXIN AND ITS USE

(75) Inventors: Lionel Breton, Versailles (FR); Florence Girerd, Paris (FR); Beatrice Renault, Saint Maurice (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/581,678

(22) PCT Filed: Dec. 18, 1998

(86) PCT No.: PCT/FR98/02796
§ 371 (c)(1),
(2), (4) Date: Oct. 10, 2000

(87) PCT Pub. No.: WO99/32078
PCT Pub. Date: Jul. 1, 1999

(30) Foreign Application Priority Data

Dec. 19, 1997 (FR) .............................. 97 16177

(51) Int. Cl.⁷ .............................. A61K 7/00; A61K 7/48
(52) U.S. Cl. .......................... 424/401; 514/53; 514/847
(58) Field of Search .................... 514/53, 538, 847; 424/401

(56) References Cited

U.S. PATENT DOCUMENTS 5,132,294 A * 7/1992 Mimura et al. ................ 514/53
5,661,179 A * 8/1997 Samid ......................... 514/538

FOREIGN PATENT DOCUMENTS

| EP | 0 060 553 | 9/1982 |
| EP | 0 103 878 | 3/1984 |
| EP | 0 451 889 | 10/1991 |
| FR | 1 269 573 | 7/1991 |
| GB | 0451889 A1 * | 3/1951 |

OTHER PUBLICATIONS

Webster's College Dictionary, forth edition, p. 1209, 2001.*
R. Rovesti: "Recherches sur l'action des auxines et des phytohormones en cosmetique", Parfumerie Mod., vol. 48, No. 54, 1956, pp. 86–91, XP002082741.

* cited by examiner

Primary Examiner—Jose' G. Dees
Assistant Examiner—M. Haghighatian
(74) Attorney, Agent, or Firm—Burns, Doane, Swecker & Mathis, L.L.P.

(57) ABSTRACT

The invention concerns the use of at least one auxin in a cosmetic composition as agent for stimulating the synthesis of skin lipids.

8 Claims, No Drawings

COSMETIC COMPOSITION CONTAINING AT LEAST ONE AUXIN AND ITS USE

The invention relates to the use of at least one auxin in a cosmetic composition, as an agent for promoting the synthesis of skin lipids.

In particular, the compositions of the invention are intended for stimulating the synthesis of the total lipids of the skin, particularly those of the epidermis.

The invention also relates to a moisturizing cosmetic composition comprising at least one auxin.

Human skin consists of two compartments, namely a deep compartment, the dermis, and a superficial compartment, the epidermis.

The dermis gives the epidermis a solid support. It is also the epidermis' nourishing factor. It consists mainly of fibroblasts and of an extracellular matrix composed mainly of collagen, elastin and a substance known as ground substance, these components being synthesized by the fibroblasts. Leukocytes, mastocytes and tissue macrophages are also found therein. It also contains blood vessels and nerve fibres.

The epidermis is in contact with the external environment. Its role consists in protecting the body against dehydration and external attack, whether this is chemical, mechanical, physical or infectious attack.

Natural human epidermis is composed mainly of three types of cells, namely keratinocytes, which form the great majority, melanocytes and Langerhans cells. Each of these cell types contributes, by virtue of its intrinsic functions, towards the essential role played in the body by the skin.

The cells constituting the epidermis are delimited by an intercellular lipid domain. During differentiation, the phospholipids, whose role is to develop the fluid structure of the cell membranes in the live layers of the epidermis, are gradually replaced with a mixture composed mainly of fatty acids, cholesterol and sphingolipids.

These lipids are organized in specific lamellar structures whose integrity depends not only on the quality of the fractions present but also on their respective proportion. This lamellar structure of the lipids in the intercellular lipid domain of the epidermis is responsible for the skin's fluidity and thus its suppleness.

The lipids are also responsible for the "barrier" properties of the epidermis, particularly of the stratum corneum.

Epidermal lipids are synthesized mainly in the live epidermis. They consist mainly of phospholipids, sphingolipids, cholesterol, free fatty acids, triglycerides and cholesterol alkyl esters.

Phospholipids are essential for making cell membranes. They play an important role in mediating extracellular signals and in forming free aliphatic chains used for the production of energy. They constitute a reservoir of free fatty acids required for making sphingolipids.

Sphingolipids (or ceramides) are essential for maintaining the multilamellar structure of the interco-neocytic lipids. They are also essential for water exchanges and for the "barrier" function of the epidermis.

Cholesterol plays a primordial role in moisturizing the skin and in the "barrier" function of the epidermis.

Free fatty acids play a major role in maintaining the lamellar structure of the lipids of the stratum corneum, but also in making cell membranes, in which they are responsible for the membrane fluidity, as well as in physiological processes such as the functioning of receptors or enzymatic activity.

The essential role played by the skin lipids and the importance of their integrity may thus be appreciated.

It is known, unfortunately, that the skin lipids, particularly the lipids of the epidermis, are influenced by genetic factors, ageing, the diet, the seasons, environmental factors, external attack and/or certain pathologies (for example scurvy or pellagra). The consequence of all these factors is to adversely affect or modify the composition of the skin lipids or to reduce their amount, which invariably leads to dry skin. It is known, for example, that the absence of the lipid component from a diet results in skin in a poor state of health. The absence of lipids leads to a general deterioration in health and particularly to the appearance of flaky skin with a concomitant increase of the increase in transepidermal water loss.

The skin lipids are thus essential for maintaining the water "barrier" of the skin.

It is also known that the lipids of the epidermis also have an influence on the activity of certain enzymes in the skin which are involved in maturation and desquamation of the stratum corneum.

Variations in the level and type of lipids present in the stratum corneum thus have an influence on the "barrier" function of the stratum corneum, the water content and the state of the skin.

It is also known that at the menopause, women complain that their skin feels tight and that it has the appearance of "dry skin", or even of the appearance of xerosis. Without wishing to establish any theory, given that skin lipids play an important role in moisturizing the skin and that the hormonal deficits associated with the menopause are accompanied by a general slowing-down in cell metabolism, it can be assumed, at any rate, that the sensation of tight skin or dry skin which women experience is linked in particular to a decrease in the amount of total lipids in the skin.

It may thus be appreciated that it is important to be able to stimulate the synthesis of skin lipids in order to maintain and/or restore their integrity so as to allow them to carry out the important roles for which they are responsible.

In this respect, the Applicant Company has discovered, surprisingly and unexpectedly, that certain plant hormones, or phytohormones, particularly auxins, have the property of stimulating the synthesis of lipids, particularly the total lipids of the skin.

Auxins are phytohormones, i.e. plant hormones in the same way as gibberellins, cytokinins, ethylene or abscissic acid.

Plant hormones are chemical messengers which serve as intermediates in intercellular communication in higher plants. They are in general relatively small molecules which act in very small amounts. Plant hormones are involved in regulating the growth processes of plants.

Auxins are plant hormones which are involved in regulating the elongation of plant cells and in the growth of plants in response to a unidirectional stimulus, this phenomenon being known as tropism (see "Plant propagation by tissue culture", George E. F. and Sherrington P. D., 1984, Exegetics Limited or "Dictionary of natural products", Chapman and Hall, 1997).

In the prior art, auxins are known for their use in regulating calcium flow across cell membranes (EP 240 257), or as forming part of anti-tumour compositions (FR 2 597 339), for treating surface wounds on the skin (EP 60 553) or for treating burns or ulcers (EP 103 878).

To the Applicant's knowledge, the use of at least one auxin to stimulate the synthesis of the total lipids of the skin has never been described in the prior art.

One subject of the invention is thus the use, in a cosmetic composition, of an effective amount of at least one auxin, the auxin or the composition being intended to stimulate the synthesis of the total lipids of the skin.

The term "auxin" is used to describe natural and/or synthetic substances which stimulate the elongation of the coleoptiles and stalks of plants.

Thus, according to the invention, the auxins can be of natural or synthetic origin.

The expression "natural auxin" means any auxin, or any preparation containing it, which is present in the natural state in at least one plant.

The expression "synthetic auxin" means any compound which has activity similar or identical to that of natural auxins, but which has been obtained by chemical synthesis or by biotechnology.

Thus, in the text hereinbelow, the term "auxin" is intended to denote a purified natural or synthetic auxin or any preparation containing a natural or synthetic auxin.

The auxins which can be used according to the invention are those described in the two reference works cited hereinabove in the text. Among these, mention may be made, for example, of 3-indolacetic acid (IAA), 4-chloro-3-indoleacetic acid (4-Cl-IAA), phenylacetic acid (PAA); 3-indolebutyric acid (IBA), 2,4-dichlorophenoxyacetic acid (2,4-D), α-naphthaleneacetic acid (α-NAA), β-naphthoxyacetic acid, indolethanol, indolacetaldehyde and indolacetonitrile.

α-Naphthoxyacetic acid is preferably used according to the invention.

Needless to say, it is possible according to the invention to use the auxins alone or as a mixture.

Particularly, the auxin or the composition containing it are used according to the invention in topical application on the skin.

It has been seen previously that lipids are involved, inter alia, in the "barrier" function of the skin, in moisturizing the skin and in the suppleness of the skin. It has also been seen that the menopause induces cutaneous effects, particularly on the skin lipids.

Thus, one of the aspects of the invention is to propose the use, in a cosmetic composition, of an effective amount of at least one auxin, the auxin or the composition being intended to reinforce the "barrier" function of the skin.

According to another aspect, the subject of the invention is the use, in a cosmetic composition, of an effective amount of at least one auxin, the auxin or the composition being intended to promote moisturization of the skin.

According to yet another aspect, a subject of the invention is the use, in a cosmetic composition, of an effective amount of at least one auxin, the auxin or the composition being intended to reinforce the suppleness of the skin.

According to yet another aspect, a subject of the invention is the use, in a cosmetic composition, of an effective amount of at least one auxin, the auxin or the composition being intended to combat the effects of the menopause on the skin, more particularly the effects of the menopause on the skin which are linked to the decrease in the amount of skin lipids.

The amount of auxin which can be used according to the invention obviously depends on the desired effect and should be an amount which is effective for stimulating the synthesis of skin lipids.

By way of example, the amount of auxin which can be used according to the invention can range, for example, from $10^{-6}\%$ to 10% and preferably from $10^{-3}\%$ to 5% of the total weight of the composition.

A subject of the invention is also a cosmetic composition intended to promote the synthesis of the total lipids of the skin, comprising, in a cosmetically acceptable medium, an effective amount of at least one auxin.

A subject of the invention is also a moisturizing cosmetic composition comprising, in a cosmetically acceptable medium, an effective amount of at least one auxin.

A subject of the invention is also a softening cosmetic composition comprising, in a cosmetically acceptable medium, an effective amount of at least one auxin.

A subject of the invention is also a cosmetic composition intended for combating the effects of the menopause on the skin, particularly the effects of the menopause on the skin lipids, comprising, in a cosmetically acceptable medium, an effective amount of at least one auxin.

Finally, a subject of the invention is a cosmetic composition intended to reinforce the "barrier" function of the skin, comprising, in a cosmetically acceptable medium, an effective amount of at least one auxin.

Preferably, in the cosmetic compositions of the invention, the auxin is β-naphthoxyacetic acid.

In these compositions, the auxin or the β-naphthoacetic acid is in an amount which is identical to that described previously in the text.

Needless to say, the composition according to the invention comprises a cosmetically acceptable support and can be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, these spherules possibly being polymeric nanoparticles such as nanospheres and nanocapsules, or better still lipid vesicles of ionic and/or nonionic type.

This composition can be more or less fluid and can have the appearance of a white or coloured cream, an ointment, a milk, a lotion, a serum, a paste or a mousse. It can optionally be applied to the skin in the form of an aerosol. It can also be in solid form, and for example in stick form. It can be used as a care product, as a cleansing product, as a make-up product or as a simple deodorant product.

In a known manner, the composition of the invention can also contain adjuvants that are common in cosmetics and dermatology, such as hydrophilic or lipophilic gelling agents, hydrophilic or lipophilic active agents, preserving agents, antioxidants, solvents, fragrances, fillers, screening agents, pigments, chelating agents, odour absorbers and dyestuffs. The amounts of these various adjuvants are those used conventionally in the fields considered and, for example, from 0.01% to 20% of the total weight of the composition. Depending on their nature, these adjuvants can be introduced into the fatty phase, into the aqueous phase, into the lipid vesicles and/or into the nanoparticles.

When the composition of the invention is an emulsion, the proportion of the fatty phase can range from 5% to 80% by weight, and preferably from 5% to 50% of the total weight of the composition. The oils, emulsifiers and co-emulsifiers used in the composition in emulsion form are chosen from those used conventionally in the field considered. The emulsifier and the co-emulsifier are present in the composition in a proportion ranging from 0.3% to 30% by weight, and preferably from 0.5% to 20% of the total weight of the composition.

As oils which can be used in the invention, mention may be made of mineral oils, oils of plant origin (apricot oil, sunflower oil), oils of animal origin, synthetic oils, silicone oils and fluoro oils (perfluoropolyethers). Fatty alcohols (cetyl alcohol), fatty acids and waxes (beeswax) can also be used as fatty substances.

As emulsifiers and co-emulsifiers which can be used in the invention, mention may be made, for example, of fatty acid esters of polyethylene glycol, such as PEG-40 stearate and PEG-100 stearate, and fatty acid esters of a polyol, such as glyceryl stearate and sorbitan tristearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

The composition can contain other hydrophilic active agents, such as proteins or protein hydrolysates, amino acids, polyols, urea, allantoin, sugars and sugar derivatives, water-soluble vitamins, plant extracts and hydroxy acids.

Lipophilic active agents which can be used are retinol (vitamin A) and its derivatives, tocopherol (vitamin E) and its derivatives, essential fatty acids, ceramides, essential oils and salicylic acid and its derivatives.

It is also possible to use, in combination with the auxin used according to the invention, compounds chosen from antibacterial agents such as macrolides, pyranosides and tetracyclines, and in particular erythromycin;

calcium antagonists such as verapamil and diltiazem;

OH-radical scavengers such as dimethyl sulphoxide;

plant extracts such as extracts from Iridacea plants or from soybean, these extracts possibly containing isoflavones;

extracts from microorganisms, in particular including bacterial extracts such as those from non-photosynthetic filamentous bacteria.

Other compounds which can also be added to the above list are, for example, potassium-channel openers such as diazoxide and minoxidil, spiroxazone, phospholipids such as lecithin, linoleic acid and linolenic acid, salicylic acid and its derivatives described in French patent FR 2 581 542, for instance salicylic acid derivatives bearing an alcanoyl group containing from 2 to 12 carbon atoms in position 5 of the benzene ring, hydroxycarboxylic or ketocarboxylic acids and their esters, lactones and their corresponding salts, anthralin, carotenoids, eicosatetraenoic acid and eicosatrienoic acid or their esters and amides, and vitamin D and its derivatives.

According to the invention, it is possible, inter alia, to combine at least one auxin with other active agents intended in particular for preventing and/or treating skin complaints. Among these active agents, mention may be made, for example, of:

agents which modify skin differentiation and/or proliferation and/or pigmentation, such as retinoic acid or its isomers, retinol and its esters, vitamin D and its derivatives, oestrogens such as oestradiol, kojic acid or hydroquinone;

anti-parasitic agents, in particular metronidazole, crotamiton or pyrethroids;

antifungal agents, in particular compounds belonging to the imidazole family, such as econazole, ketoconazole and miconazole or their salts, polyene compounds such as amphotericin B, compounds of the allylamine family, such as terbinafine, or octopirox;

antiviral agents such as acyclovir;

steroidal anti-inflammatory agents, such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anaesthetics such as lidocaine hydrochloride and its derivatives;

anti-pruriginous agents such as thenaldine, trimeprazine or cyproheptadine;

keratolytic agents such as α- and β-hydroxycarboxylic or β-keto carboxylic acids, their salts, amides or esters, and more particularly hydroxy acids such as glycolic acid, lactic acid, salicylic acid, citric acid and fruit acids in general, and 5-n-octanoylsalicylic acid;

free radical scavengers, such as α-tocopherol or its esters, superoxide dismutases, certain metal-chelating agents or ascorbic acid and its esters;

antiseborrhoeic agents such as progesterone;

antidandruff agents such as octopirox or zinc pyrithione;

anti-acne agents such as retinoic acid aor benzoyl peroxide;

substances such as antagonists of substance P, of CGRP or of bradykinin or NO synthase inhibitors, these compounds being described as being active in the treatment of sensitive skin and as having anti-irritant effects, in particular with respect to any irritant compounds which may be present in the compositions.

Thus, another subject of the invention relates to a composition comprising an effective amount of at least one auxin and at least one agent chosen from antibacterial agents, antiparasitic agents, antifungal agents, antiviral agents, anti-inflammotory agents, anti-pruriginous agents, anaesthetics, keratolytic agents, free-radical scavengers, anti-seborrhoeic agents, antidandruff agents, anti-acne agents, agents for modifying skin differentiation and/or proliferation and/or pigmentation, antagonists of substance P, of CGRP or of bradykinin, or NO synthase inhibitors.

Active agents which can be used in particular are moisturizers such as polyols (for example glycerol), vitamins (for example D-panthenol), anti-inflammatory agents, calmants (allantoin, cornflower water), UVA and UVB screening agents, matt-effect agents (for example the partially crosslinked polyorganodimethylsiloxanes sold under the name KSG® by Shin Etsu), and mixtures thereof.

Agents which may also be added are anti-wrinkle active agents, and in particular tensioning products such as plant proteins and their hydrolysates, in particular the soybean protein extract sold under the name Eleseryl® by the company LSN or the oat derivative sold under the name Reductine® by the company Silab.

Needless to say, the auxins can be used in the preparation of cosmetic and/or pharmaceutical compositions, particularly dermatological compositions, intended for stimulating lipid synthesis.

Other characteristics and advantages of the invention will emerge more clearly from the examples which follow, which are given for illustrative purposes and without any limitation. In the text hereinabove and hereinbelow, the proportions are given as a percentage by weight, except where otherwise indicated.

EXAMPLE 1

Study of the effect of β-naphthoxyacetic acid on the synthesis of the total lipids of the skin.

The study is carried out by measuring the incorporation of acetate labelled with carbon-14 in models of reconstructed human epidermis sold by the company Skinethic, the total lipids composition of which is close to that of normal human epidermis.

The reconstructed human epidermis is cultured according to the supplier's recommendations.

β-Naphthoxyacetic acid, at concentrations of $10^{-5}$, $10^{-6}$, and $10^{-7}$ M, is placed in contact for 72 hours with reconstructed human epidermides, after culturing the latter for 14 days under the conditions recommended by the supplier. The labelling with $^{14}$C-acetate (sodium [2-$^{14}$C]-acetate sold by Amersham, 59 mci/mmol) is carried out 24 hours after placing the test product in contact with the culture, i.e. during the final 48 hours of culturing, at a rate of 0.5 μCi of $^{14}$C-acetate per culture.

At the end of culturing, after washing the epidermides with phosphate buffer (PBS), the epidermides are dissociated and the cells are lysed with 0.5 M perchloric acid from ice. The lysates then undergo an extraction with a methanol/chloroform mixture (2:1), a centrifugation and a re-extraction of the pellets obtained, under the same conditions as above. The lipids are separated by addition of PBS and chloroform (Blight-Byer technique). The organic phase containing the lipids is taken and the radioactivity incorporated into this phase is determined by liquid scintillation. The organic phase is then dried under a flow of nitrogen. A thin layer chromatography on plates on plates (Merck K60) using, as eluent, a chloroform/methanol/water mixture (50:18:2.6) to separate the phospholipids, or a hexane/ether/acetic acid mixture (15:5.6:0.19) to separate the neutral lipids.

The plates are then autoradiographed for 24 hours and the chromatograms are analysed by densitometry using the One-D-Scan software from the company Scanalytics.

The results are evaluated relative to a control consisting of cells which have not been treated with β-naphthoxyacetic acid.

A positive control ($10^{-4}$ M trifluoperazine), which is known to stimulate lipid synthesis, and an negative control ($10^{-6}$ M retinoic acid) are introduced into the test by way of reference.

The results of this test, expressed as a percentage of stimulation, are given in the table below.

| Treatment | % |
|---|---|
| Untreated cells | 100 |
| $10^{-5}$ M β-Naphthoxyacetic acid | 110 |
| $10^{-6}$ M β-Naphthoxyacetic acid | 113 |
| $10^{-7}$ M β-Naphthoxyacetic acid | 116 |
| $10^{-4}$ M Trifluoroperazine | 122 |
| $10^{-6}$ M Retinoic acid | 82 |

These results show that β-naphthoxyacetic acid significantly stimulates the incorporation of acetate, showing an effect on lipid synthesis.

EXAMPLE 2

Examples of compositions according to the invention. These compositions are obtained by the usual techniques commonly used in cosmetics or pharmacy.

| Composition 1: care cream | |
|---|---|
| Beeswax | 1.5% |
| Apricot kernel oil | 13.0% |
| Fragrance | 0.4% |
| β-Naphthoxyacetic acid | 0.01% |
| Xanthan | 0.5% |
| Cyclopentadimethylsiloxane | 5.0% |
| Sterilized demineralized water | 69.29% |
| Sucrose mono-di-palmitostearate | 3.0% |
| Methylglucose sesquistearate | 3.0% |
| Stearic acid | 1.0% |
| Cetyl alcohol | 3.0% |
| Preserving agents | 0.3% |
| Composition 2: Body oil | |
| Liquid petroleum jelly | 47.99% |
| Apricot kernel oil | 6.0% |
| Fragrance | 1.0% |
| β-Naphthoxyacetic acid | 0.01% |
| Cyclopentadimethylsiloxane | 45.0% |
| Composition 3: Make-up-removing milk | |
| 2-Ethylhexyl palmitate | 10.5% |
| Liquid fraction of karite butter | 16.5% |
| Preserving agents | 0.3% |
| Fragrance | 0.15% |
| β-Naphthoxyacetic acid | 0.01% |
| Sodium hydroxide | 0.04% |
| Carboxyvinyl polymer | 0.2% |
| Sterilized demineralized water | 69.8% |
| Mixture of cetylstearyl glucoside and of cetyl alcohol and stearyl alcohol | 2.5% |
| Composition 4: Care cream | |
| Beeswax | 1.5% |
| Apricot kernel oil | 13.0% |
| Preserving agents | 0.3% |
| Fragrance | 0.4% |
| Triethanolamine | 0.17% |
| β-Naphthoxyacetic acid | 0.01% |
| 2,4-Dichlorophenoxyacetic acid | 0.01% |
| Xanthan | 0.5% |
| Cyclopentadimethylsiloxane | 5.0% |
| Sterilized demineralized water | 69.28% |
| Sucrose mono-di-palmitostearate | 3.0% |
| Methylglucose sesquistearate | 3.0% |

What is claimed is:

1. A method for improving or reinforcing the barrier function of skin comprising administering an effective amount of at least one auxin to an individual in need of such improvement or reinforcement.

2. The method according to claim 1, wherein the auxin is administered alone or in a composition used in topical application on the skin.

3. The method according to claim 1, wherein the auxin is selected from the group consisting of indolacetic acid (IAA), 4-chloro-3-indoleacetic acid (4-Cl-IAA), phenylacetic acid (PAA), 3-indolebutyric acid (IBA), 2,4-dichlorophenoxyacetic acid (2,4-D), α-napthaleneacetic acid (α-NAA), β-naphthoxyacetic acid, indolethanol, indolacetaldehyde and indolacetonitrile.

4. The method according to claim 3, wherein the auxin is β-naphthoxyacetic acid.

5. The method according to claim 4, wherein the auxin is administered alone or in a composition present in an amount ranging from $10^{-6}$% to 10% of the total weight of the composition.

6. The method according to claim 5, wherein the auxin is present in an amount ranging from $10^{-5}$% to 5% of the total weight of the composition.

7. A method for improving or promoting moisturization of skin comprising administering an effective amount of at least one auxin to an individual in need of such improvement or promotion.

8. A method for the stimulation of lipid synthesis in the skin comprising administering an effective amount of at least one auxin to an individual in need of such stimulation.

* * * * *